United States Patent [19]

Heyd et al.

[11] 4,315,779
[45] Feb. 16, 1982

[54] NON-ADHESIVE GEL COMPOSITIONS FOR STABILIZING DENTURES

[75] Inventors: Allen Heyd, Norwalk, Conn.; Nutan B. Shah, New Rochelle, N.Y.

[73] Assignee: Richardson-Vicks Inc., Wilton, Conn.

[21] Appl. No.: 80,583

[22] Filed: Oct. 1, 1979

[51] Int. Cl.$^3$ .......................... A61C 13/22; C08L 1/28; C08L 5/00; C08L 5/04

[52] U.S. Cl. ...................................... 106/35; 106/189; 106/208

[58] Field of Search .................. 106/35, 189, 205, 208

[56] References Cited

U.S. PATENT DOCUMENTS 2,716,615  8/1955  Voris .................................. 106/189

FOREIGN PATENT DOCUMENTS 967751  8/1964  United Kingdom .................. 106/35

OTHER PUBLICATIONS

Webster's Third New International Dictionary, G & C Merriam Company, Springfield, Mass., 1963, p. 601.
Hackh's Chemical Dictionary, Fourth Edition, McGraw-Hill Book Company, N.Y.C., 1969, p. 202.

Primary Examiner—Allan Lieberman
Attorney, Agent, or Firm—George W. Rauchfuss, Jr.

[57] ABSTRACT

A substantially non-adhesive gel composition for use in improving the fit and adaptation of dentures to the oral cavity of the user, which comprises about 1 to 10% by weight of a hydrophilic cellulose polymer or alginate, about 5 to about 40% by weight of a demulcent, preferably glycerine, and about 50 to about 95% water. The composition reduces denture movement and prevents buildup of undesirable deposit such as plaque or the like.

8 Claims, No Drawings

NON-ADHESIVE GEL COMPOSITIONS FOR STABILIZING DENTURES

FIELD OF THE INVENTION

The invention relates to a substantially non-adhesive gel composition and its use in improving the fit, adaptation and physical and chemical environment of dentures in the oral cavity of the user.

BACKGROUND OF THE INVENTION

A large proportion of the population are denture wearers. The prosthetic appliance in denture wearers covers a large portion of the oral mucous membranes, especially those of the maxilla. Although the adaptation of the denture appliance to the oral cavity can be improved by the use of denture adhesives, the adaptation is gradually lowered with the passage of time due in part to the breakdown of the denture adhesive or change in the oral cavity. Moreover a substantial number of denture wearers do not or will not employ denture adhesives for various reasons. Additionally, many denture wearers keep their dentures in the oral cavity twenty-four hours a day and, in so doing, the covered mucous membranes or tissues do not benefit from the cleansing action of the tongue, mechanical cleansing action during mastication, or from the buffering and cleansing action of saliva.

These patterns of use among denture wearers have led to various undesirable consequences. Among such consequences which have been documented in numerous studies published in the scientific literature, there may be mentioned, for example, tissue inflammation caused by instability, trauma and stress as a result of the loss of adaptation of the denture to the oral cavity; pain, discomfort and irritation caused by food particles becoming lodged beneath the denture appliance; the buildup of bacteria as well as the development of pathological yeasts, such as *Candida albicans*, whose combined endotoxins or metabolic products are potential inflammatory products which can also result in denture stomatitis; odor and taste problems resulting from stagnant areas beneath the dentures and from by-products of bacterial and yeast metabolism; slipping and sliding of the dentures during mastication resulting in inflammation and soreness; and inflammation, soreness or disease caused by the breakdown of the natural and physiological environment of the oral cavity and the mucous membranes thereof simply by the presence of the denture appliance in the oral cavity covering the mucous membranes for prolonged periods of time.

In the past, certain temporary measures have been utilized to alleviate the distress caused by ill-fitting dentures. Among these may be mentioned various pastes employing gum arabic as the base material or elastic polymeric compositions of polyacrylic ester and polyvinyl acetate or polyvinyl chloride with a low molecular weight plasticizer. However, none of these has been entirely acceptable and they fail to provide the required degree of maintenance of the natural and physiological environment in the oral cavity of denture wearers. Moreover, numerous denture wearers who do not use denture adhesives for one reason or another object to said compositions for the same or similar reasons. There is therefore a need for a suitable composition which alleviates or eliminates most or all of these undesirable features and problems.

SUMMARY OF THE INVENTION

It has now been discovered that a denture composition comprising about 1 to about 10% by weight hydrophilic cellulose polymer or alginate, about 5 to about 40% by weight demulcent selected from glycerine, sorbitol, and propylene glycol and about 50 to about 95% by weight water provides such a composition which alleviates or eliminates to a substantial degree most or all of the undesirable features and problems encountered with the use of heretofore know denture compositions. Moreover, the compositions of this invention help to maintain the natural and physiological environment in the oral cavity when dentures are being worn. In a preferred form of the invention, the hydrophilic cellulose polymer is employed in a cross-linked form and the composition takes the form of a substantially non-adhesive cohesive gel.

DETAILED DESCRIPTION OF THE INVENTION

The denture compositions of this invention can employ any suitable hydrophilic cellulose polymer or alginate. Especially suitable are the normally solid particulate or powdered synthetic cellulose polymers or gums such as for example, methylcellulose, ethylcellulose, methylethylcellulose, carboxymethylcellulose, hydroxyethylcellulose, hydroxypropylcellulose and the like as well as the water soluble salts of the cellulose polymers, such as for example, sodium carboxymethylcellulose, sodium carboxyethylcellulose and sodium carboxymethylhydroxyethylcellulose. Also useful are the particulate or powdered gums known as KELCO polymers. The KELCO polymers are: (1) alginic acid and its salts also known as Kelco Algins or Kelgin, (2) organic derivatives of alginic acid also known as propylene glycol alginates or Kelcoloid and, (3) xanthan gums also known as Keltrol or Kelzan. All these gums are carbohydrates or, specifically, polysaccharides. They are available as dry powders from Kelco Company, San Diego, Calif.

Kelco Algin or Kelgin is reported to be hydrophilic inorganic derivatives of alginic acid. It is a complex polysaccharide gum and chemically is believed to be composed of polymannuronic acid and polyguluronic acid. The monomers are linked together by beta linkages to form a high molecular weight polymer.

Kelcoloid is an organic derivative of alginic acid as opposed to Kelco Algin which is an inorganic derivative, specifically, monovalent salts of the alginic acid. A typical Kelcoloid is propylene glycol alginate. Keltrol or Kelzan is xanthan gum which is a natural biopolysaccharide. The polymeric molecule is composed of monosaccharides such as mannose, glucose and guluronic acid. The xanthan gum can be called a block polymer of five sugar units, and one guluronic acid unit. The main chain of xanthan gum is built up of $\beta$-D-glucose units linked through the 1- and 4-positions giving rise to chemical structure of the main chain of xanthan gum identical to the chemical structure of cellulose. Although about 1 to about 10% by weight alginate is employed in denture compositions of this invention, preferably about 1 to about 5% by weight alginate is employed if a high molecular weight alginate is employed. The amount of cellulose or alginate employed in the compositions of this invention can be from about 1 to about 10% by weight, preferably about 1 to about 5% and most preferably about 2 to about 3%.

A preferred hydrophilic polymer employed in the compositions of this invention is a cross-linked cellulose polymer, such as for example, sodium carboxymethylcellulose cross-linked in a known manner with aluminum sulfate and citric acid. Crosslinking of the cellulose polymer can also be accomplished with equimolor amounts of water soluble salts of chromium or ferric cation such as chromium or ferric chloride or the like, employed in place of the aluminum sulfate. When the cross-linked form of cellulose polymer is employed, it is generally desirable to cross-link the cellulose polymer with about 10 to 25% by weight of aluminum sulfate and about 5 to 10% by weight of aluminum sulfate and about 5 to 10% by weight of citric acid based on the weight of cellulose polymer employed. When aluminum sulfate and citric acid are employed as the cross-linking agents for the cellulose polymer, they may be employed in the following amounts by weight based on the total weight of the compositions of this invention: aluminum sulfate in an amount up to about 0.5% and citric acid in an amount up to about 1.5%.

As demulcents in the compositions of this invention, there may be employed for example glycerine, sorbitol or propylene glycol and preferably glycerine in amounts of about 5 to about 40% by weight, preferably about 20 to about 30% by weight and most preferably about 25% by weight.

The compositions of this invention can vary from hypotonic to moderately hypertonic and the appropriate amount of sodium chloride can be added to the composition to adjust the tonicity of the composition.

The composition of the present invention will generally have a pH in the range of from about 6.0 to about 7.5, preferably from about 7.0 to 7.5 and most preferably about 7.0 and any suitable orally acceptable buffering agents may be employed, such as for example, sodium and potassium mono- and dibasic phosphate salts and the like.

The compositions of this invention can also have incorporated therein preservatives, antimicrobial agents, dyes and flavors in generally used amounts.

The compositions of this invention are generally characterized by having a product viscosity in the range of from about 25,000 to about 200,000 cps at room temperature, having an elastic memory and being non-sticky. The compositions are also characterized by being antibacterial or bacteriostatic and/or mycostatic or mycocidal against *Candida albicans*, all of which can play a pathogenic role in denture stomatitis.

In use in the oral cavity as adaptive compositions for dentures, the compositions provide a cushioning effect which takes pressure off the gums and provides a demulcent action that soothes both healthy and irritated gums. The compositions also enhance the stability of the dentures in the oral cavity yet do not stick to the dentures or mucuous tissues of the oral cavity. Additionally, the compositions of this invention prevent harmful deposits from building up beneath the denture surfaces, reduce odor and reduce or prevent tenderness and irritation of tissue. The compositions also provide a cooling and soothing effect on the oral tissue. And, as previously mentioned, the compositions of this invention maintain the natural and physiological environment in the oral cavity when the dentures are being worn and a composition of this invention is being employed.

Preferred compositions of this invention are characterized by the following general formula:

| Component | % Wt/Wt |
|---|---|
| Sodium carboxymethylcellulose | 1 to 5% |
| Glycerine | 20 to 30% |
| Aluminum sulfate | 0 to 0.5% |
| Citric Acid | 0 to 1.5% |
| Water and optional components | Balance |

An even more preferred composition of this invention is the following formula:

| Component | % Wt/Wt |
|---|---|
| Sodium carboxymethylcellulose | 3.0% |
| Glycerine | 25.0% |
| Aluminum sulfate, 18 $H_2O$ | 0.5% |
| Citric Acid, hydrous | 0.135% |
| Water and optional components | Balance |

A still, even more preferred composition of this invention is a composition of the formula:

| Component | % Wt/Wt |
|---|---|
| Sodium carboxymethylcellulose | 2.0% |
| Glycerine | 25.0% |
| Methylparaben | 0.05% |
| Propylparaben | 0.05% |
| Aluminum sulfate, anhydrous | 0.28% |
| Citric acid, hydrous | 0.135% |
| Sodium chloride | 0.50% |
| Hydrochloric acid | 0.24% |
| Sodium hydroxide | 0.227% |
| Dyes and flavors | 0.602% |
| Water | 71.132% |

It is preferred that when a cross-linked cellulose polymer is employed in the compositions of this invention that the cross-linking be in situ, that is, in the compounding of the composition of the invention.

For example, the most preferred composition of this invention, as set forth hereinbefore, is compounded in the following exemplary manner.

In any suitable size stainless steel tank, the glycerin is added and the propylparaben, methylparaben and sodium carboxymethylcellulose are slowly added with stirring over a period of about fifteen minutes until a smooth slurry is obtained.

Into another suitable vessel, add approximately 2.4% of the total water employed and slowly add the hydrochloric acid and add any dyes to the acidified water. Add the dyed acidified water with mixing to another vessel containing approximately 84.5% of the total water employed. Next add the slurry containing the glycerine and sodium carboxymethylcellulose with adequate agitation and mix for about an hour until a uniform gum is obtained.

In another suitable vessel, add, in order, the citric acid, aluminum sulfate and sodium chloride into approximately 11.4% of the total water employed and mix to dissolve the components. Separately dissolve the sodium hydroxide in about 1.6% of the total water employed and add to the citric acid containing solution with mixing until a uniform solution of pH about 7.15 is obtained and thereafter add this resulting solution with agitation to the uniform gum previously obtained and continue the agitation for about an hour. Thereafter flavoring agents as desired may be added to the product and the product mixed thoroughly. If desired the product can be processed through any suitable homogenizer, such as for example, a Versator, to improve the homogenization of the product.

It will be fully appreciated that the foregoing description and examples are merely illustrative of the invention and that modifications thereof by one skilled in the art can be made without departing from the spirit and scope of the invention.

We claim:

1. A substantially non-adhesive gel composition for improving the adaptation of dentures to the oral cavity of the wearer thereof, comprising about 1 to about 10% by weight of a hydrophilic cellulose polymer, an alginate or xanthan gum, from about 5 to about 40% by weight of a demulcent selected from the group consisting of glycerine, sorbitol and propylene glycol and from about 50 to about 95% by weight water.

2. A composition of claim 1 wherein the demulcent is glycerine.

3. A composition of claim 1 wherein the hydrophilic cellulose polymer is cross-linked sodium carboxymethylcellulose.

4. A composition of claim 2 wherein the hydrophilic cellulose polymer is a cross-linked sodium carboxymethylcellulose.

5. A composition of claim 3 wherein the sodium carboxymethylcellulose is cross-linked with aluminum sulfate and citric acid.

6. A composition of claim 4 wherein the sodium carboxymethylcellulose is cross-linked with aluminum sulfate and citric acid.

7. A composition of claim 2 having the formula:

| Component | % Wt/Wt |
|---|---|
| Sodium carboxymethylcellulose | 1 to 5% |
| Glycerine | 20 to 30% |
| Aluminum sulfate | 0 to 0.5% |
| Citric Acid | 0 to 1.5% |
| Water and optional components | Balance |

8. A composition of claim 2 having the following formula:

| Component | % Wt/Wt |
|---|---|
| Sodium carboxymethylcellulose | 2.0% |
| Glycerine | 25.0% |
| Preservative agents | 0.1% |
| Aluminum sulfate | 0.28% |
| Citric Acid | 0.135% |
| Sodium Chloride | 0.50% |
| Hydrochloric Acid | 0.24% |
| Sodium Hydroxide | 0.227% |
| Dyes and flavoring agents | 0.602% |
| Water | 71.132% |

* * * * *